United States Patent [19]

Altenburger et al.

[11] Patent Number: 5,739,382
[45] Date of Patent: Apr. 14, 1998

[54] DERIVATIVES OF 2-AMINOBENZENESULPHONIC ACID AND OF 2-AMINOBENZENESULPHONYL CHLORIDE, THEIR PREPARATION AND THEIR USE AS SYNTHETIC INTERMEDIATES

[75] Inventors: Jean Michel Altenburger, Meudon; Gilbert Lassalle, Clamart, both of France

[73] Assignee: Synthelabo, Le Plessis Robinson Cedex, France

[21] Appl. No.: 796,481

[22] Filed: Feb. 10, 1997

Related U.S. Application Data

[62] Division of Ser. No. 562,455, Nov. 24, 1995.

[30] Foreign Application Priority Data

Nov. 25, 1994 [FR] France .................................. 94 14129

[51] Int. Cl.⁶ .................................................. C07C 309/46
[52] U.S. Cl. .................................. 562/59; 562/58; 562/73; 562/832
[58] Field of Search ............................. 562/73, 59, 58, 562/832

[56] References Cited

U.S. PATENT DOCUMENTS 2,794,833  6/1957  Merian .

*Primary Examiner*—Robert Gerstl
*Attorney, Agent, or Firm*—Jacobson, Price, Holman & Stern, PLLC

[57] ABSTRACT

The present invention provides a compound of formula (1)

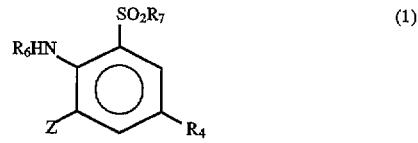

in which:

$R_4$ represents a hydrogen atom, a halogen atom or a nitro group;

$R_6$ represents a hydrogen atom or a straight or branched ($C_1$–$C_6$)alkyl group;

$R_7$ represents a chlorine atom or a hydroxyl group; and

Z represents: a phenyl group optionally substituted with one or more halogen atoms, straight or branched ($C_1$–$C_4$)alkyl groups, straight or branched ($C_1$–$C_4$) alkoxy groups, or trifluoromethyl, formyl, —$CH_2OR$, —$CH_2OCOR$, —$CH_2CONRR'$, —$CH_2ONCOR$, —COOR, nitro, —NHR, —NRR' or —NHCOR groups, wherein R and R' are each, independently, a hydrogen atom or a ($C_1$–$C_7$)alkyl group; a heterocyclic group optionally substituted as defined above for phenyl; or a cyclo($C_5$–$C_8$)alkyl group; additionally, when $R_7$ represents chlorine, Z can represent iodine; in the free form or in the form of a salt with an alkali metal or tertiary amine, processes for their preparation and their use as synthetic intermediates.

4 Claims, No Drawings

DERIVATIVES OF 2-AMINOBENZENESULPHONIC ACID AND OF 2-AMINOBENZENESULPHONYL CHLORIDE, THEIR PREPARATION AND THEIR USE AS SYNTHETIC INTERMEDIATES

This is a divisional of application Ser. No. 08/562,455, filed Nov. 24, 1995, allowed.

The invention relates to derivatives of 2aminobenzenesulphonic acid and of 2-aminobenzenesulphonyl chloride, to their preparation and to their use as synthetic intermediates.

The present invention provides a compound of formula (1)

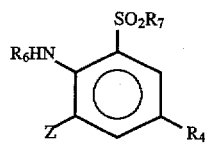

in which:

$R_4$ represents a hydrogen atom, a halogen atom or a nitro group;

$R_6$ represents a hydrogen atom or a straight or branched ($C_1$–$C_6$)alkyl group;

$R_7$ represents a chlorine atom or a hydroxyl group; and

Z represents: a phenyl group optionally substituted with one or more halogen atoms, straight or branched ($C_1$–$C_4$)alkyl groups, straight or branched ($C_1$–$C_4$) alkoxy groups, or trifluoromethyl, formyl, —CH$_2$OR, —CH$_2$OCOR, —CH$_2$CONRR', —CH$_2$ONCOR, —COOR, nitro, —NHR, —NRR' or —NHCOR groups, wherein R and R' are each, independently, a hydrogen atom or a ($C_1$–$C_7$)alkyl group; a heterocyclic group optionally substituted as defined above for phenyl; or a cyclo($C_5$–$C_8$)alkyl group; additionally, when $R_7$ represents chlorine, Z can represent iodine; in the free form or in the form of a salt with an alkali metal or tertiary amine.

Examples of heterocyclic groups are pyridyl, thienyl, furyl, thiazolyl and pyrimidyl groups.

The present invention also provides a process for the preparation of a compound of formula (1) in which Z represents an iodine atom and $R_7$ represents a chlorine atom in which process the corresponding sulphonic acid is reacted with a chlorinating agent such as sulphuryl chloride in the presence of triphenylphosphine, or dichlorotriphenylphosphorane, in the presence of a base such as tributylamine, in an aprotic solvent such as dichloromethane.

The present invention also provides a process for the preparation of a compound of formula (1) in which Z represents: a phenyl group optionally substituted with one or more halogen atoms, straight or branched ($C_1$–$C_4$)alkyl groups, straight or branched ($C_1$–$C_4$)alkoxy groups, or trifluoromethyl, formyl, —CH$_2$OR, —CH$_2$OCOR, —CH$_2$CONRR', —CH$_2$ONCOR, —COOR, nitro, —NHR, —NRR', or —NHCOR groups, wherein R and R' are each, independently, a hydrogen atom or a ($C_1$–$C_7$)alkyl group; or a heterocyclic group such as pyridyl, thienyl, furyl, thiazolyl and pyrimidyl, optionally substituted as defined above for phenyl; $R_7$ is a chlorine atom and $R_4$ and $R_6$ are as defined above. These compounds correspond to those of formula (1a), in which A is equal to Z. They may be synthesized according to Scheme 1.

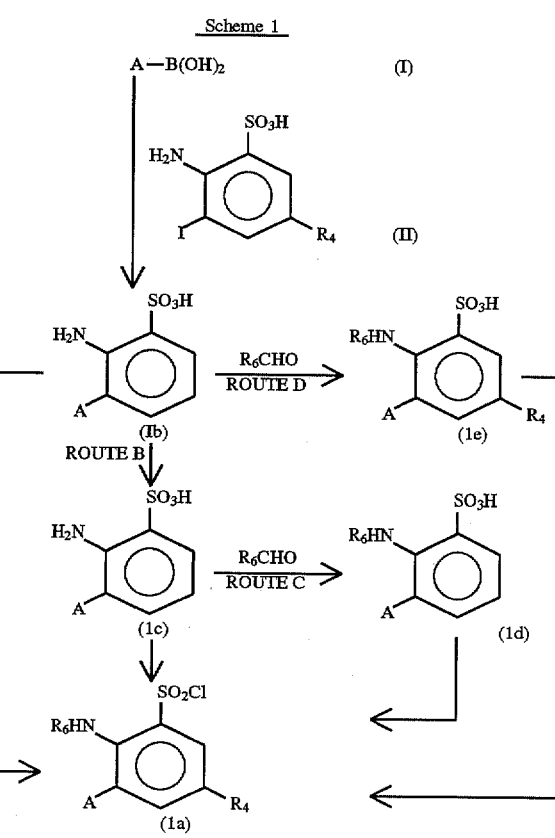

A boron derivative of formula (II), in which A is as defined above, is condensed with a derivative of formula (III), in which $R_4$ represents a halogen atom, generally in the presence of a catalyst such as tetrakis(triphenylphosphine) palladium (0) and a base such as sodium carbonate or triethylamine, in a protic or aprotic solvent (such as 1,2-dimethoxyethane) to form a compound of formula (1b) which corresponds to a compound of formula (1) in which $R_6$ is a hydrogen atom and $R_7$ is a hydroxyl group. Next, route A: either the compound of formula (1b) is reacted with a chlorinating agent such as sulphuryl chloride in the presence of triphenylphosphine, or dichlorotriphenylphosphorane, generally in an aprotic solvent such as dichloromethane, in the presence of a base such as tributylamine to form a compound of formula (1a), in which $R_6$ is a hydrogen atom and $R_4$ is a halogen atom, route B: or the compound of formula (1b) is subjected to a hydrogenolysis to form a compound of formula (1c), which corresponds to a compound of formula (1) in which $R_4$ and $R_6$ each represent a hydrogen atom and $R_7$ represents a hydroxyl group, followed either by treating the compound of formula (1c) according to the method described above to form a compound of formula (1a), in which $R_4$ and $R_6$ each represent a hydrogen atom, or by reacting the compound of formula (1c) with an aldehyde of formula $R_6$CHO, wherein $R_6$ represents a straight or branched ($C_1$–$C_6$)alkyl group, generally in an acidic medium, in the presence of sodium cyanoborohydride (route C) to form a compound of formula (1d) which corresponds to a compound of formula (1) in which $R_4$ represents a hydrogen atom, $R_6$ represents a straight or branched ($C_1$–$C_6$) alkyl group and $R_7$ represents a hydroxyl group, and then, starting with the compound of formula (1d), using a chlorinating agent such as dichlorotriphenylphosphorane according to the method described above, a compound of formula (1a) is prepared in which $R_4$ represents a hydrogen atom and $R_6$ represents a straight or branched ($C_1$–$C_6$)alkyl group route D: or the compound of formula (1b) is reacted with an aldehyde of formula $R_6$CHO, wherein $R_6$ represents a straight or branched ($C_1$–$C_6$)alkyl group, generally in an acidic medium, in the presence of sodium cyanoborohydride to form a compound of formula (1e), which corresponds to a compound of formula (1) in which $R_4$ represents a halogen atom, $R_6$ represents a straight or branched ($C_1$–$C_6$)alkyl group and $R_7$ represents a hydroxyl group, from which a compound of formula (1a), in which $R_6$ represents a straight or branched ($C_1$–$C_6$)alkyl group and $R_4$ represents a halogen atom, is prepared, using a chlorinating agent such as dichlorotriphenylphosphorane according to the method described above.

In a variant of the process, the compounds of formula (1b) may be prepared from a derivative of formula A-Sn(R)$_3$ (II') where R is a ($C_1$–$C_4$)alkyl group, which is reacted with a compound of formula (III), in the form of the triethylamine salt, generally in the presence of a catalyst such as tetrakis (triphenylphosphine)palladium (0), in a protic or aprotic solvent such as dimethylformamide.

The compounds of formula (1) in which $R_4$ represents a nitro group are synthesized according to Scheme 1 (route A) starting with 2-amino-3-iodo-5-nitrobenzenesulphonic acid.

The compounds of formula (1) in which Z represents a phenyl group or a heterocycle substituted with an amino group are generally prepared by reduction of the corresponding compound for which Z is a phenyl group or a heterocycle substituted with a nitro group.

The compounds of formula (1) in which Z represents a phenyl group or a heterocycle substituted with a group —COOH are generally prepared by oxidation of the corresponding compound for which Z is a phenyl group or a heterocycle substituted with a formyl group.

The compounds of formula (1) in which Z represents a phenyl group or a heterocycle substituted with a hydroxymethyl group are generally prepared by reduction of the corresponding compound for which Z is a phenyl group or a heterocycle substituted with a formyl group.

The compounds of formula (1) in which Z represents a phenyl group or a heterocycle substituted with an electrophilic group are generally prepared from the corresponding compound for which Z is a phenyl group or an unsubstituted heterocycle.

The compounds according to the invention for which Z represents a cyclo($C_5$–$C_8$)alkyl group and $R_4$ represents a hydrogen atom correspond to formula (1f) and may be synthesized according to Scheme 2.

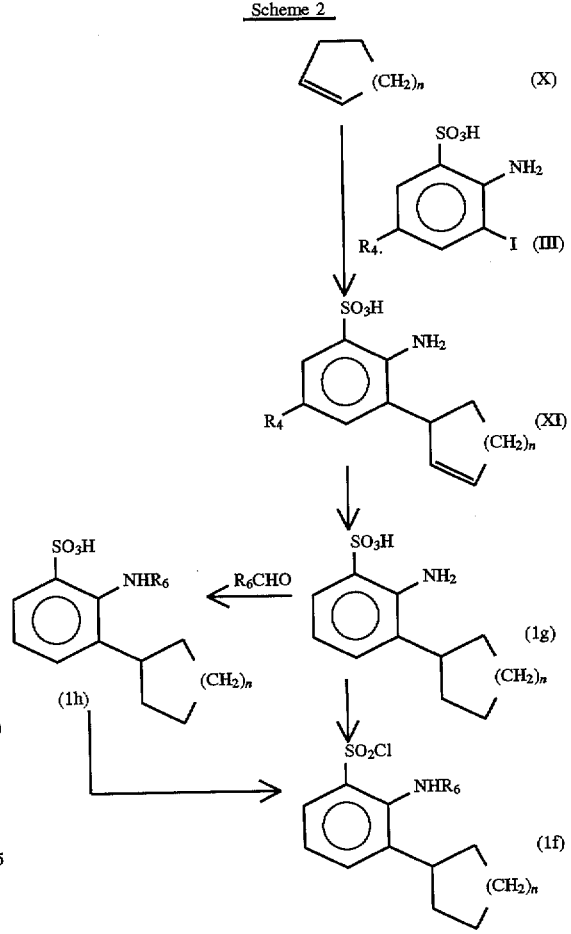

Scheme 2

A cyclo($C_5$–$C_8$)alkenyl of formula (X), in which n is equal to 1, 2, 3 or 4, is reacted with a compound of formula (III), in which $R_4$ represents a halogen atom, generally in the presence of a base such as sodium acetate or potassium acetate, in an aprotic solvent such as dimethylformamide, to form a compound of formula (XI), which is subjected to catalytic hydrogenation to obtain a compound of formula (1g) which corresponds to a compound of formula (1) in which $R_4$ and $R_6$ represent a hydrogen atom and $R_7$ represents a hydroxyl group; next, either the compound of formula (1g) is treated with a chlorinating agent such as dichlorotriphenylphosphorane according to the method described above to form a compound of formula (1f), in which $R_6$ represents a hydrogen atom and n is equal to 1, 2, 3 or 4, or the compound of formula (1g) is reacted with an aldehyde of formula $R_6$CHO, wherein $R_6$ represents a straight or branched ($C_1$–$C_6$)alkyl group, generally in an acidic medium, in the presence of sodium cyanoborohydride, to form a compound of formula (1h), which corresponds to a compound of formula (1) in which $R_4$ represents a hydrogen atom, $R_6$ represents a straight or branched ($C_1$–$C_6$)alkyl group and $R_7$ represents a hydroxyl group, from which a compound of formula (1f), in which $R_6$ represents a straight or branched ($C_1$–$C_6$)alkyl group and n is equal to 1, 2, 3 or 4, is prepared, using a chlorinating agent such as dichlorotriphenylphosphorane according to the method described above.

The starting compounds are commercially available or are described in the literature or may be prepared according to methods which are described therein or which are known to those skilled in the art.

Thus, 2-amino-5-nitro-3-iodobenzenesulphonic acid is generally prepared from 2-amino-5-nitro-3-benzenesulphonic acid according to the method described by Boyle et al. in J. Chem. Soc., (1919), 119, 1505.

Examples 1 to 18 which follow illustrate the preparation of certain compounds in accordance with the invention.

Example A illustrates the use of the compounds of formula (1) as synthetic intermediates.

The microanalyses and the IR and NMR spectra confirm the structure of the compounds obtained.

The compound numbers in the examples refer to those in the table given later, which illustrates the chemical structures and the physical properties of a few compounds according to the invention.

Example 1 (Compound No. 1)
2-amino-5-bromo[1,1'-biphenyl]-3-sulphonic acid
1.1. 2-amino-5-bromo-3-iodobenzenesulphonic acid
 1.1.1. 2-amino-5-bromobenzenesulphonic acid A mixture containing 31 g (180 mmol) of 4-bromoaniline and 9.7 ml (220 mmol) of sulphuric acid in 200 ml of 1,2-dichlorobenzene is heated at 180° C. for 6 hours. The reaction medium is allowed to cool to room temperature and is then filtered. The residue is washed with dichloromethane.

45 g of product are obtained, which product is used without further purification in the following step.

Melting point=>240° C.
Yield=97%
 1.1.2. 2-amino-5-bromo-3-iodobenzenesulphonic acid To 45 g (176 mmol) of 2-amino-5-bromobenzenesulphonic acid are added 46 g (282 mmol) of iodine chloride, 400 ml of aqueous 1N hydrochloric acid solution and 400 ml of methanol. The mixture is heated at 90° C. for 18 hours and concentrated under reduced pressure, and the residue is crystallized from ethanol.

41 g of product are obtained, which product is used without further purification in the following step.

Melting point=240° C. (decomposition)
Yield=62%
1.2. 2-amino-5-bromo[1,1'-biphenyl]-3-sulphonic acid To a mixture of 37.8 g (100 mmol) of 2-amino-5-bromo-3-iodobenzenesulphonic acid and 32 g (300 mmol) of sodium carbonate in 300 ml of 1,2-dimethoxyethane and 150 ml of water are successively added, under a nitrogen atmosphere, 5.8 g (5 mmol) of tetrakis(triphenylphosphine) palladium (0) and 19.5 g (160 mmol) of benzeneboronic acid. The mixture is heated at the reflux temperature for 4 hours and the reaction medium is then concentrated under reduced pressure. The residue thus obtained is then dissolved in a mixture containing 300 ml of methanol, 300 ml of 0.1N hydrochloric acid and 16 ml of 95% sulphuric acid. The mixture is concentrated to 100 ml under reduced pressure, cooled to 0° C. and filtered. The residue is purified by chromatography on an RP 18 reverse-phase column, eluting with an acetonitrile:water mixture (2:8).

20 g of product are obtained after recrystallization from an ethanol/ether mixture.
Yield=60%
Melting point=197.5° C.

Example 2 (Compound No. 2)
2-amino[1,1'-biphenyl]-3-sulphonic acid Route B 20 g (61 mmol) of 2-amino-5-bromo[1,1'-biphenyl]-3-sulphonic acid is placed in the presence of 3 g of 10% palladium-on-charcoal in a mixture containing 40 ml of ethanol and 100 ml of acetic acid, in a Parr apparatus. The reaction medium is heated to 50° C. under a pressure of 0.35 MPa (50 psi), it is filtered through Celite and the filtrate is concentrated under reduced pressure. The residue is recrystallized from an ethanol/ether mixture.

10 g of product are obtained.
Yield=66%
Melting point=241.5° C.

Example 3 (Compound No. 3)
2-amino[1,1'-biphenyl]-3-sulphonyl chloride Route B

To a solution of 4.95 g (18.9 mmol) of triphenylphosphine in 20 ml of dichloromethane are added dropwise, at 0° C. under a nitrogen atmosphere, 1.44 ml (18 mmol) of sulphuryl chloride. The reaction medium is left stirring for 10 minutes at 0° C., followed by addition over 5 minutes of a solution containing 2.24 g (9 mmol) of 2-amino[1,1'-biphenyl]-3-sulphonic acid and 2.14 ml (9 mmol) of tributylamine in 9 ml of dichloromethane. The mixture is brought to room temperature, left stirring at this temperature for 3 hours and purified by chromatography on a column of silica gel, eluting with a pentane:dichloromethane mixture (8:2).

1.9 g of product are obtained.
Yield=80%
IR, oil, cm$^{-1}$: 3495; 3394; 3079; 3028; 1614; 1564; 1467; 1436; 1360; 1231; 1170; 1152; 1073; 1015; 839; 786; 760; 739; 704; 662.
$^1$H NMR, CDCl$_3$, ppm, 200 MHz: 7.8 (1H, dd, J=8 Hz, J=1.5 Hz); 7.55-7.3 (6H, m); 6.8 (1H, t, J=8 Hz); 5.35 (2H, s).

Example 4 (Compound No. 4)
2-(propylamino)[1,1'-biphenyl]-3-sulphonic acid Route D To a solution containing 5 g (0.02 mol) of 2-amino[1,1'-biphenyl]-3-sulphonic acid, 3.6 ml (0.05 mol) of propanaldehyde and 3.28 g (0.02 mol) of sodium acetate in 60 ml of water and 15 ml of acetic acid is added dropwise a solution of 1.9 g (0.03 mol) of sodium cyanoborohydride in 15 ml of water. The reaction medium is left stirring for 3 hours at room temperature, and is concentrated and acidified with 80 ml of 1N hydrochloric acid solution and 2 ml of 95% sulphuric acid solution. The solution is cooled to 0° C. and filtered.

5 g of product are obtained after recrystallization from an ethanol/ether mixture.
Yield=85%
Melting point=213.5° C.

Example 5 (Compound No. 5)
2-(propylamino)[1,1'-biphenyl]-3-sulphonyl chloride Route D To a solution of 8.2 g (28 mmol) of 2-(propylamino)[1,1'-biphenyl]-3-sulphonic acid and 6.7 ml (28 mmol) of tributylamine in 14 ml of dichloromethane is added dropwise, at 0° C. under a nitrogen atmosphere, a solution of 16.95 g (42 mmol) of dichlorotriphenylphosphorane in 75 ml of dichloromethane. The reaction medium is brought to room temperature and kept stirring at this temperature for 6 hours. It is purified by chromatography on a florisil® column, eluting with ether.

4.35 g of product are obtained in the form of a yellow oil.
Yield=50%

IR, oil, cm$^{-1}$: 3411; 3027; 2963; 2933; 2875; 1586; 1514; 1466; 1416; 1363; 1281; 1264; 1246; 1163; 1106; 1018; 798; 783; 760; 739; 702.

$^1$H NMR, CDCl$_3$, ppm, 200 MHz: 7.9 (1H, dd, J=8 Hz, J=1.7 Hz); 7.6-7.2 (6H, m); 6.9 (1H, t, J=7.6 Hz); 5.6 (1H, s); 2.6-2.5 (2H, m); 1.5-1.35 (2H, m); 0.7 (3H, t, J=7.2 Hz).

Example 6 (Compound No. 14)

Sodium 2-amino-5-bromo-3'-formyl[1,1'-biphenyl]-3-sulphonate

A mixture of 11.34 g (30 mmol) of 2-amino-5-bromo-3-iodobenzenesulphonic acid, 4.5 g (30 mmol) of 3-formylbenzeneboronic acid, 10.5 g (99 mmol) of sodium carbonate and 1.73 g (1.5 mmol) of tetrakis(triphenylphosphine)palladium (0) in 40 ml of dimethylformamide and 20 ml of water is heated at 70° C. under argon for 5 hours. The reaction medium is then concentrated under reduced pressure and the residue is purified by chromatography on an RP 18 column, eluting with a water-acetonitrile mixture (8:2).

7.4 g of product are obtained in the form of a white powder.
Yield=65%
Melting point=164°–168° C.

Example 7 (Compound No. 15)

N,N,-diethylethanamine salt of 2-amino-3'-formyl[1,1'-biphenyl]-3-sulphonic acid A mixture of 3.5 g (9.3 mmol) of sodium 2-amino-5-bromo-3'-formyl[1,1'-biphenyl]-3-sulphonate, 4.7 g (74.4 mmol) of ammonium formate, 1.1 g (11.2 mmol) of potassium acetate and 0.75 g (0.65 mmol) of tetrakis(triphenylphosphine)palladium (0) in 20 ml of dimethylformamide is heated at 75° C. for 7 hours. The reaction medium is then concentrated under reduced pressure and the residue is purified by chromatography on an RP 18 column, eluting with a water/acetonitrile mixture (8:2). The product is recrystallized from an ethanol/ether mixture.

1.2 g of product are obtained in sodium salt form, in the form of a white powder.
Yield=43%

The N,N-diethylethanamine salt is prepared according to methods known to those skilled in the art.
Melting point=70°–76° C.

Example 8 (Compound No. 16)

2-amino-5-bromo-3'-nitro[1,1'-biphenyl]-3-sulphonic acid

To a solution of 1.9 g (5 mmol) of 2-amino-5-bromo-3-iodobenzenesulphonic acid and 1.6 g (15 mmol) of sodium carbonate in 25 ml of dimethylformamide and 12.5 ml of water are added successively, under a nitrogen atmosphere, 0.231 g (0.2 mmol) of tetrakis(triphenylphosphine)palladium (0) and 1.42 g (8.5 mmol) of 3-nitrobenzeneboronic acid. The reaction medium is heated for 2 hours at 70° C. and is concentrated under reduced pressure. The residue thus obtained is purified by chromatography on an RP 18 reverse-phase column, eluting with an acetonitrile/water mixture (1:9). 1.5 g of compound are obtained in sodium sulphonate form.

The acid is freed by crystallization of 1.5 g of sodium sulphonate from 80 ml of methanol to which are added 5 ml of 1N hydrochloric acid and 0.267 µl of sulphuric acid. The mixture is concentrated, cooled to 0° C., filtered, washed and concentrated under reduced pressure. The product is recrystallized from an ethanol/ether mixture.

1.3 g of product are obtained in the form of a yellow powder.
Yield=70%
Melting point=205° C.

Example 9 (Compound No. 17)

2-amino-3'-nitro[1,1'-biphenyl]-3-sulphonic acid

A mixture of 8 g (20 mmol) of sodium 2-amino-5-bromo-3'-nitro[1,1'-biphenyl]-3-sulphonate, 7.6 g (120 mmol) of ammonium formate, 2.35 g (24 mmol) of potassium acetate and 1.38 g (1.2 mmol) of tetrakis(triphenylphosphine) palladium (0) in dimethylformamide is heated at 75° C. for 8 hours. The reaction medium is then concentrated under reduced pressure and the residue is purified by chromatography on an RP 18 column, eluting with a water/acetonitrile mixture (8:2). The product is recrystallized from an ethanol/ether mixture.

2.2 g of product are obtained in sodium salt form in the form of a white powder.

The acid is prepared according to the methods known to those skilled in the art.
Yield=35%
Melting point=228°–234° C.

Example 10 (Compound No. 19)

Sodium 2-amino-5-bromo-3-(2-thienyl)benzenesulphonate

A mixture of 36 g (95.3 mmol) of 2-amino-5-bromo-3-iodobenzenesulphonic acid and 12.2 g (95.3 mmol) of 2-thienylboronic acid in 140 ml of 1,2-dimethoxyethane in the presence of 5.5 g of tetrakis(triphenylphosphine) palladium (0) and 30.3 g of sodium carbonate is heated at 70°–75° C. for 8.5 hours. The solvent is evaporated off under vacuum, the mixture is cooled to 0° C. and washed with water to pH=7, and the residue is then taken up in an ether/ethanol mixture (95:5).

21 g of product are obtained.
Yield=72%
Melting point=208°–214° C.

Example 11 (Compound No. 20)

Sodium 2-amino-3-(2-thienyl)benzenesulphonate 21 g (59 mmol) of sodium 2-amino-5-bromo-3-(2-thienyl)benzenesulphonate are heated at 100° C. for 1 hour in the presence of 350 ml of 10% sodium hydroxide solution, 15 ml of ethanol and 7.4 g of zinc. The temperature of the reaction medium is allowed to return to room temperature and 300 ml of methanol are added. The mixture is filtered through Celite, the filtrate is concentrated and the residue is taken up in 1N sodium hydroxide solution at 0° C. and dried under vacuum.

13 g of product are obtained.
Yield=75%
Melting point=224° C.

Example 12 (Compound No. 22)

N,N-diethylethanamine salt of 2-amino-3-(5-chloro-2-thienyl)benzenesulphonic acid To a solution of 2.57 g (9.4 mmol) of 2-amino-3-(2-thienyl)benzenesulphonyl chloride in 10 ml of dichloromethane is added dropwise 0.824 ml (10.3 mmol) of sulphuryl chloride and the mixture is left stirring for 5 hours at 0° C. The reaction medium is then concentrated under reduced pressure, the residue is taken up in 40 ml of dioxane, 20 ml of aqueous 1N sodium hydroxide solution are added at 0° C. and the mixture is left stirring for 4 hours at 0° C. The reaction medium is concentrated and filtered, and the precipitate is washed and dried under reduced pressure.

2.5 g of product are obtained in sodium salt form.
Yield=86%

To a solution of 2.1 g (6.7 mmol) of the sodium salt of 2-amino-5-bromo-3-(2-furyl)benzene sulphonate in 50 ml of methanol are added, at 0° C., 7 ml of hydrochloric acid and 0.36 ml of concentrated sulphuric acid. The mixture is concentrated under reduced pressure and is cooled to 0° C. The residue is filtered off, washed and dried under reduced pressure. The acid is then converted into the N,N-diethylethanamine salt according to methods known to those skilled in the art.

After crystallization from an ethyl acetate/ether mixture, 1.99 g of product are obtained.
Melting point=139.4° C.

Example 13 (Compound No. 27)
N,N-diethylethanamine salt of 2-amino-5-bromo-3-(2-furyl) benzenesulphonic acid A mixture of 14.4 g (30 mmol) of the N,N-diethylethanamine salt of 2-amino-5-bromo-3-iodobenzenesulphonic acid, 9.92 ml (31.5 mmol) of 2-(tributylstannyl)furan, 0.29 g (1.5 mmol) of copper iodide and 1.73 g (1.5 mmol) of tetrakis(triphenylphosphine) palladium (0) in 30 ml of dimethylformamide is heated at 95° C. for 7 hours. The reaction medium is then concentrated under reduced pressure and the residue is purified by chromatography on a column of silica gel, eluting with a methanol/dichloromethane/triethylamine mixture (2:98:0.005), and the product is recrystallized from ethyl acetate.

6.8 g of product are obtained in triethylamine form in the form of orange-coloured crystals.
Yield=54%
Melting point=93°–98° C.

Example 14 (Compound No. 28)
2-amino-5-bromo-3-(2-furyl)benzenesulphonic acid To a solution of 10 g (23.8 mmol) of the N,N-diethylethanamine salt of 2-amino-5-bromo-3-(2-furyl) benzenesulphonic acid in 100 ml of methanol are added, at 0° C., 24 ml of aqueous 1N hydrochloric acid solution and 1.3 ml of concentrated sulphuric acid. The mixture is concentrated under reduced pressure to about 20 ml and is cooled to 0° C. The precipitate is filtered off, washed with water and dried under reduced pressure. The product is recrystallized from an ethanol/ether mixture.

6.3 g of product are obtained in acid form, in the form of a white powder.
Yield=83%
Melting point=252° C. (melting with decomposition)

Example 15 (Compound No. 29)
N,N-diethylethanamine salt of 2-amino-3-(2-furyl) benzenesulphonic acid A mixture of 5.6 g (18 mmol) of 2-amino-5-bromo-3-(2-furyl)benzenesulphonic acid, 5.6 g (90 mmol) of ammonium formate, 3.5 g (36 mmol) of potassium acetate and 1.04 g (0.9 mmol) of tetrakis(triphenylphosphine)palladium (0) in 20 ml of dimethylformamide is heated to 85° C. The mixture is left stirring for 1 hour at this temperature and the reaction medium is then concentrated under reduced pressure. The residue is purified by chromatography on an RP 18 column, eluting with a water/acetonitrile mixture (8:2).

3 g of product are obtained in potassium salt form, in the form of an orange-coloured powder.
Yield=62%

To a solution of 4.4 g (16 mmol) of potassium salt in 100 ml of methanol are successively added, at 0° C., 20 ml of 1N hydrochloric acid solution and 0.85 ml of concentrated sulphuric acid solution, and the mixture is concentrated under reduced pressure. The mixture is cooled to 0° C., filtered, washed and dried under reduced pressure. 3.4 g of product are obtained.
Yield=90%

The N,N'-diethylethanamine salt is prepared by methods known to those skilled in the art.

$^1$H NMR, CDCl$_3$, ppm, 200 MHz: 7.8 (dd, 1H, J=7.3 Hz, J=1.8 Hz); 7.55-7.45 (m, 2H); 6.75 (t, 1H, J=7 Hz); 6.62 (dd, 1H, J=3.6 Hz, J=0.8 Hz); 6.55 (dd, 1H, J=5.5 Hz, J=2 Hz); 5.75 (s, 2H); 3.15 (q, 6H, J=6.0 Hz); 1.35 (t, 9H, J=6.0 Hz)

Example 16 (Compound No. 32)
2-amino-3-cyclopentylbenzenesulphonic acid 7.1. 2-amino-5-bromo-3-cyclopent-2-en-1-ylbenzenesulphonic acid A mixture containing 30 g (79.4 mmol) of 2-amino-5-bromo-3-iodobenzenesulphonic acid, 35 ml (397 mmol) of cyclopentene, 19.5 g (199 mmol) of potassium acetate, 6.24 g (23.8 mmol) of triphenylphosphine and 2.67 g (11.9 mmol) of palladium (II) acetate in 160 ml of N,N-dimethylformamide is heated at 80° C. for 48 hours, under a nitrogen atmosphere. The reaction medium is then concentrated under reduced pressure and the residue is taken up in a mixture containing 200 ml of methanol, 200 ml of 1N hydrochloric acid and 10 ml of 95% sulphuric acid solution. The mixture is evaporated again under reduced pressure and filtered, and the precipitate thus obtained is purified by chromatography on an RP 18 reverse-phase column, eluting with an acetonitrile/water mixture (3:7). The residue is recrystallized from a methanol/pentane mixture.

14.9 g of product are obtained, which product is used without further purification in the following step.
Yield=60%

7.2. 2-amino-3-cyclopentylbenzenesulphonic acid 9.6 g (30.3 mmol) of 2-amino-5-bromo-3-cyclopent-2-en-1-ylbenzenesulphonic acid are placed in a Parr apparatus and 1 g of 10% palladium-on-charcoal, 80 ml of methanol, 10 ml of acetic acid and 50 ml of water are added. The reaction medium is heated to 50° C. under a pressure of 0.35 MPa (50 psi). It is filtered through Celite, the filtrate is concentrated under reduced pressure and the residue thus obtained is crystallized from a methanol/pentane mixture.

4.9 g of product are obtained.
Yield=67%
Melting point=>250° C.

Example 17 (Compound No. 33)
2-amino-3-cyclopentylbenzenesulphonyl chloride

To a solution of 2.42 g (9.2 mmol) of triphenylphosphine in 5 ml of dichloromethane is added dropwise, at 0° C. under a nitrogen atmosphere, 0.70 ml (8.8 mmol) of sulphuryl chloride. The reaction medium is left stirring for 10 minutes at 0° C., followed by addition over 5 minutes of a solution containing 1.06 g (4.4 mmol) of 2-amino-3-cyclopentylbenzenesulphonic acid and 1.04 ml of tributylamine in 3 ml of dichloromethane. The mixture is brought to room temperature and is left at this temperature for 2 hours, then it is purified by chromatography on a column of silica gel, eluting with a dichloromethane/pentane mixture (1:1).

0.8 g of product is obtained in the form of a viscous yellow oil.

Yield=80%

IR, oil, cm$^{-1}$: 3507; 3408; 2954; 2869; 1628; 1565; 1470; 1357; 1158; 836; 739.

$^1$H NMR, CDCl$_3$, ppm, 200 MHz: 7.7 (1H, d, J=8.0 Hz); 7.4 (1H, d, J=8.3 Hz); 6.8 (1H, t, J=7.8 Hz); 5.4 (2H, s); 3.1-2.9 (1H, m); 2.3-1.5 (8H, m).

Example 18 (Compound No. 34)
2-amino-5-bromo-3-iodobenzenesulphonyl chloride To a solution containing 7.6 g (20 mmol) of 2-amino-5-bromo-3-iodobenzenesulphonic acid and 4.8 ml (20 mmol) of tributylamine in 20 ml of dichloromethane is added dropwise, at 0° C. under a nitrogen atmosphere, a solution of dichlorotriphenylphosphorane (9.7 g (37.5 mmol) in 45 ml of dichloromethane). The mixture is brought to room temperature, stirring is continued for 18 hours and the product is purified by chromatography on a column of silica gel, eluting with a dichloromethane/pentane mixture (2:8).

6 g of product are obtained in the form of yellow crystals.

Yield=75%

Melting point=78° C.

$^{1H}$ NMR, CDCl$_3$, ppm, 200 MHz: 8.05 (1H, d, J=2.65 Hz); 7.95 (1H, d, J=2.65 Hz); 5.8 (2H, s).

Key to the Table

In the "Salt" column: 'N(C$_2$H$_5$)$_3$' represents an N,N-diethylethanamine salt, 'Na' represents a sodium salt and the absence of any mention means that the compound is in free form.

In the "Melting point or NMR" column: 'a' NMR in methyl-d$_6$ sulphoxide (DMSO-d$_6$); '(d)' corresponds to melting with decomposition

TABLE

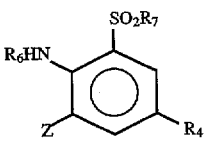

(1)

| No. | R$_6$ | R$_4$ | R$_7$ | Z | Salt | Melting point (°C.) $^1$H NMR CDCl$_3$, ppm, 200 MHz |
|---|---|---|---|---|---|---|
| 1 | —H | —Br | —OH | 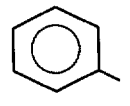 | — | 197.5 |
| 2 | —H | —H | —OH | 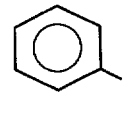 | — | 241.5 |
| 3 | —H | —H | —Cl | 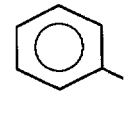 | — | 7.8(1H, dd, J=8Hz, J=1.5Hz); 7.55–7.3(6H, m); 6.8 (1H, t, J=8Hz); 5.35(2H, s) |
| 4 | —CH$_2$CH$_2$CH$_3$ | —H | —OH | 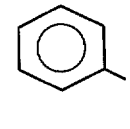 | — | 213.5 |
| 5 | —CH$_2$CH$_2$CH$_3$ | —H | —Cl | 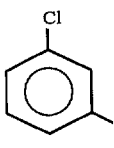 | — | 7.9(1H, dd, J=8Hz, J=1.7Hz); 7.6–7.2(6H, m); 6.9(1H, t, J=7.6Hz); 5.6 (1H, s); 2.6–2.5(2H, m); 1.5–1.35(2H, m); 0.7(3H, t, J=7.2Hz) |
| 6 | —H | —H | —OH | 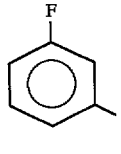 | — | 175 |
| 7 | —H | —H | —OH |  | — | 7.7(dd, 1H, J=8.5Hz, J=0.8Hz); 7.6–7.4(m, 1H); 7.3–7.1(m, 4H); 6.95(t, 1H, J=8.5Hz) |

TABLE-continued
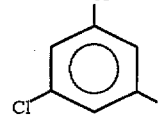
| No. | R₆ | R₄ | R₇ | Z | Salt | Melting point (°C.) $^1$H NMR CDCl₃, ppm, 200 MHz |
|---|---|---|---|---|---|---|
| 8 | —H | —Br | —OH | 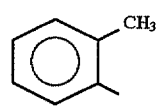 | N(C₂H₅)₃ | 7.75(dd, 1H, J=8.6Hz, J=0.7Hz); 7.35(s, 2H); 7.25(s, 1H); 7.05(dd, 1H, J=8.6Hz, J=0.7Hz); 5.05(s, 2H) 6.7 (t, 1H, J=8.6Hz); 3.15(q, 6H, J=6Hz); 1.35(t, 9H, J=6Hz) |
| 9 | —H | —H | —OH | 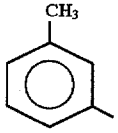 | N(C₂H₅)₃ | 7.7(dd, 1H, J=8.1Hz, J=0.6Hz); 7.3–7.05(m, 4H); 6.95(dd, 1H, J=8.1Hz, J=0.6Hz); 6.65(t, 1H, J=8.1Hz); 4.75(s, 2H); 3.1(q, 6H, J=6Hz); 2.1 (s, 3H); 1.25(t, 9H, J=6Hz) |
| 10 | —H | —H | —OH | 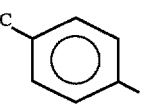 | — | 180 |
| 11 | —H | —H | —OH | 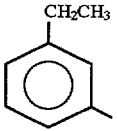 | N(C₂H₅)₃ | 7.75(dd, 1H, J=8.5Hz, J=0.7Hz); 7.35–7.2 (m, 4H); 7.05(dd, 1H, J=8.5Hz, J=0.7Hz); 6.7(t, 1H, J=8.5Hz); 5.05(s, 2H); 4.6–4.4(m, 1H); 3.1(q, 6H, J=6Hz); 2.3(s, 3H); 1.3(t, 9H, J=6Hz) |
| 12 | —H | —H | —OH | 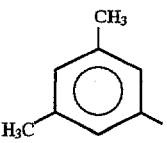 | — | 185 |
| 13 | —H | —H | —OH | 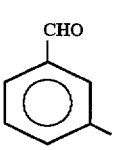 | — | >300 |
| 14 | —H | —Br | —OH | 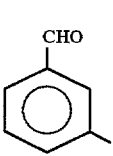 | Na | 164–168 |
| 15 | —H | —H | —OH | 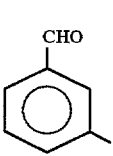 | N(C₂H₅)₃ | 70–76 |

TABLE-continued
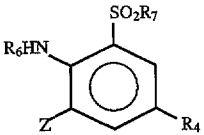
| No. | R₆ | R₄ | R₇ | Z | Salt | Melting point (°C.) $^1$H NMR CDCl$_3$, ppm, 200 MHz |
|---|---|---|---|---|---|---|
| 16 | —H | —Br | —OH | 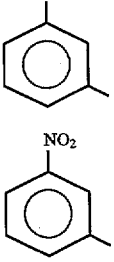 3-NO₂-phenyl | — | 205 |
| 17 | —H | —H | —OH | 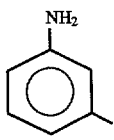 3-NO₂-phenyl | — | 228–234 |
| 18 | —H | —H | —OH | 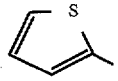 3-NH₂-phenyl | —Na | 7.5(dd, 1H, J=8Hz, J=0.2Hz); 7.15(t, 1H, J=8Hz); 6.9(dd, 1H, J=8Hz); 6.7–6.5(m, 4H) |
| 19 | —H | —Br | —OH | 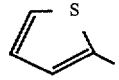 2-thienyl | Na | 208–214 |
| 20 | —H | —H | —OH | 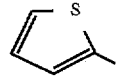 2-thienyl | Na | 224 |
| 21 | —CH₂CH₂CH₃ | —H | —OH | 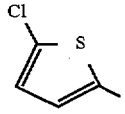 2-thienyl | Na | 88–92 |
| 22 | —H | —H | —OH | 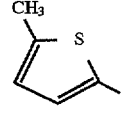 5-Cl-2-thienyl | N(C₂H₅)₃ | 139.4 |
| 23 | —H | —H | —OH | 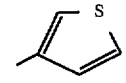 5-CH₃-2-thienyl | Na | 265–270(d) |
| 24 | —H | —H | —OH | 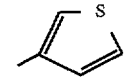 3-thienyl | Na | 220 |
| 25 | —H | —H | —Cl | 3-thienyl | — | 98.6 |
| 26 | —H | —Br | —OH | 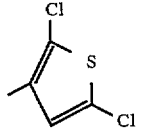 2,5-diCl-thienyl | Na | 234–238 |
| 27 | —H | —Br | —OH | 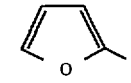 2-furyl | N(C₂H₅)₃ | 93–98 |

TABLE-continued $$\underset{Z}{\overset{R_6HN}{\bigcirc}}\overset{SO_2R_7}{\underset{R_4}{\bigcirc}} \quad (1)$$

| No. | $R_6$ | $R_4$ | $R_7$ | Z | Salt | Melting point (°C.) $^1$H NMR CDCl$_3$, ppm, 200 MHz |
|---|---|---|---|---|---|---|
| 28 | —H | —Br | —OH | furan-2-yl | — | 252(d) |
| 29 | —H | —H | —OH | furan-2-yl | N(C$_2$H$_5$)$_3$ | 7.8(dd, 1H, J=7.3Hz, J=1.8Hz); 7.55–7.45(m, 2H); 6.75(t, 1H, J=7Hz); 6.62(dd, 1H, J=3.6Hz, J=0.8Hz); 6.55(dd, 1H, J=5.5Hz, J=2Hz); 5.75(s, 2H); 3.15(q, 6H, J=6.0Hz); 1.35(t, 9H, J=6.0Hz) |
| 30 | —H | —Br | —OH | pyridin-2-yl | N(C$_2$H$_5$)$_3$ | 8.7(dd, 1H, J=6Hz, J=0.2Hz); 8–7.8(m, 2H); 7.7(d, 1H, J=0.6Hz); 7.6 (d, 1H, J=0.6Hz); 7.45–7.30(m, 1H); 7.1(s, 2H); 3.15(q, 6H, J=6Hz); 1.2 (t, 9H, J=6Hz) |
| 31 | —H | —H | —OH | pyridin-3-yl | — | 272–278 |
| 32 | —H | —H | —OH | cyclopentyl | — | >250 |
| 33 | —H | —H | —Cl | cyclopentyl | — | 7.7(1H, d, J=8.0Hz); 7.4 (1H, d, J=8.3Hz); 6.8(1H, t, J=7.8Hz); 5.4(2H, s); 3.1–2.9(1H, m); 2.3–1.5 (8H, m) |
| 34 | —H | —Br | —Cl | —I | — | 78 |
| 35 | —CH$_3$ | —H | —OH | phenyl | — | 174 |
| 36 | —CH$_2$CH$_3$ | —H | —OH | phenyl | — | 7.89(dd, 1H); 7.52(m, 6H); 7.40(dd, 1H); 5.50(broad s, 1H exchangeable); 2.95(q, 2H); 1(t, 3H) |
| 37 | —CH$_2$CH$_2$CH$_2$CH$_3$ | —H | —OH | phenyl | N(C$_2$H$_5$)$_3$ | 7.8(dd, 1H, J=8Hz, J=0, 5Hz) 7.55–7.45(m, 2H); 7.4–7.3(m, 2H); 7.3–7.2 (m, 1H); 7.15(dd, 1H, J=8Hz, J=0, 5Hz); 6.8(t, 1H, J=8Hz); 3.2(t, 6H, J=7Hz); 2.55(t, 2H, J=7Hz); 1.45–1.25(m, 13H); 1.2–1.0(m, 4H); 0.75(t, 3H, J=6Hz) |

TABLE-continued

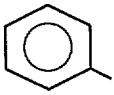

| No. | R₆ | R₄ | R₇ | Z | Salt | Melting point (°C.) $^1$H NMR CDCl$_3$, ppm, 200 MHz |
|---|---|---|---|---|---|---|
| 38 | —CH$_2$CH(CH$_3$)$_2$ | —H | —OH | (phenyl) | — | 192 |

The present invention also provides the use of a compound of formula (1) as an intermediate in the synthesis of a compound having antithrombotic activity of formula (I)

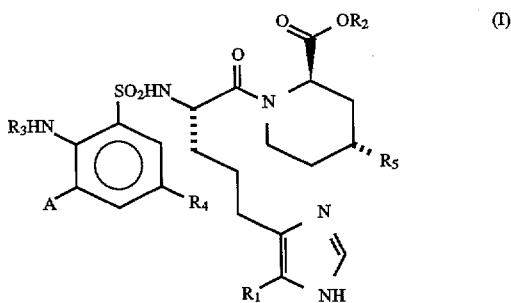

in which:

R$_1$ represents a hydrogen atom or a (C$_1$–C$_4$)alkyl group,

R$_2$ represents a hydrogen atom or a straight or branched (C$_1$–C$_4$)alkyl group;

R$_3$ represents a hydrogen atom or a straight or branched (C$_1$–C$_6$)alkyl group;

R$_4$ represents a hydrogen atom, a halogen atom or a nitro group;

R$_5$ represents a hydrogen atom or a straight or branched (C$_1$–C$_4$)alkyl group; and A represents: a phenyl group optionally substituted with a fluorine atom, a straight or branched (C$_1$–C$_4$)alkyl group, an amino group or a trifluoromethyl group; a cyclo(C$_5$–C$_8$)alkyl group; or a heterocyclic group.

Example A which follows illustrates the synthesis of the compounds of formula (I) starting with the compounds of the invention, without limiting this synthesis.

Example A
Ethyl [2R-[1(S), 2α, 4β]]-1-[2-[[2-amino[1,1'-biphenyl]-3-yl)sulphonyl]amino]-5-(1H-imidazol-4(5)-yl)-1-oxopentyl]-4-methylpiperidine-2-carboxylate hydrochloride
A.1. Ethyl [2R-[1(S), 2α, 4β]]-1-[2-[[2-amino[1,1'-biphenyl]-3-yl)sulphonyl]amino]-1-oxo-5-[1-(triphenylmethyl)-1H-imidazol-4-yl]pentyl]-4-methylpiperidine-2-carboxylate To a suspension of 1.8 g (3 mmol) of ethyl [2R-[1(S), 2α, 4β]]-1-[2-amino-1-oxo-5-[1-(triphenylmethyl)-1H-imidazol-4-yl]pentyl]-4-methylpiperidine-2-carboxylate hydrochloride and 9.2 ml (6.6 mmol) of triethylamine in 12 ml of dichloromethane is added dropwise, at 0° C. under a nitrogen atmosphere, 0.88 g (3.3 mmol) of 2-amino[1,1'-biphenyl]-3-sulphonyl chloride dissolved in 3 ml of dichloromethane. The reaction medium is left stirring at this temperature for 6 hours and is then concentrated under reduced pressure. The residue thus obtained is purified by chromatography on a column of silica gel, eluting with a methanol/dichloromethane mixture (1:99).

2 g of product are obtained.
Yield=83%
Melting point=66° C.

A.2 Ethyl [2R-[1(S), 2α, 4β]]-1-[2-[[(2-amino[1,1'-biphenyl]-3-yl)sulphonyl]amino]-5-(1H-imidazol-4(5)-yl)-1-oxopentyl]-4-methylpiperidine-2-carboxylate hydrochloride To a solution of 0.398 g (0.5 mmol) of ethyl [2R-[1(S), 2α, 4β]]-1-[2-[[(2-amino[1,1'-biphenyl]-3-yl)sulphonyl]amino]-1-oxo-5-[1-(triphenylmethyl)-1H-imidazol-4-yl]pentyl]-4-methylpiperidine-2-carboxylate and 0.16 g (1.5 mmol) of anisole in 15.5 ml of dichloromethane are added dropwise, at 0° C., 1.5 ml of trifluoroacetic acid. The temperature of the mixture is then allowed to return to room temperature, and the mixture is stirred for 7 hours at this temperature and concentrated under reduced pressure. The residue is taken up in 50 ml of ethyl acetate, treated with 50 ml of saturated sodium hydrogen carbonate solution, dried over magnesium sulphate and concentrated under reduced pressure. The final residue is purified by chromatography on a column of silica gel, eluting with a methanol/dichloromethane mixture (5:95).

0.24 g of product is obtained in base form.
Yield=80%

The hydrochloride is prepared by placing 0.24 g (0.3 mmol) of base in 5 ml of a solution of isopropanol in 0.1N hydrochloric acid and evaporating under reduced pressure. 0.24 g of product is obtained in hydrochloride form.

Melting point=108° C.
[α]$_d^{20}$97.5° (c=0.2; methanol)

The compounds of formula (I) display antithrombotic activity and are described in French Patent Application No. 94/14130.

We claim:
1. A compound of formula (1)

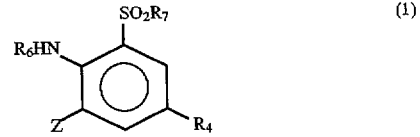

in which:

R$_4$ represents a hydrogen atom, a halogen atom or a nitro group;

$R_6$ represents a hydrogen atom or a straight or branched $(C_1-C_6)$alkyl group;

$R_7$ represents a chlorine atom or a hydroxyl group; and

Z represents: a phenyl group optionally substituted with one or more halogen atoms, straight or branched $(C_1-C_4)$alkyl groups, straight or branched $(C_1-C_4)$ alkoxy groups, or trifluoromethyl, formyl, —CH$_2$OR, —CH$_2$OCOR, —CH$_2$CONRR', —CH$_2$ONCOR, —COOR, nitro, —NHR, —NRR' or —NHCOR groups, wherein R and R' are each, independently, a hydrogen atom or a $(C_1-C_7)$alkyl group; or a cyclo $(C_5-C_8)$alkyl group; additionally, when $R_7$ represents chlorine, Z can represent iodine; in the free form or in the form of a salt with an alkali metal or tertiary amine.

2. A compound of formula (1) as claimed in claim 1 in which $R_7$ represents chlorine and Z represents iodine.

3. A compound of formula (1) as claimed in claim 1 in which Z represents: a phenyl group optionally substituted with one or more halogen atoms, straight or branched $(C_1-C_4)$alkyl groups, straight or branched $(C_1-C_4)$alkoxy groups, or trifluoromethyl, formyl, —CH$_2$OR, —CH$_2$OCOR, —CH$_2$CONRR', —CH$_2$ONCOR, —COOR, nitro, —NHR, —NRR' or —NHCOR groups, wherein R and R' are each, independently, a hydrogen atom or a $(C_1-C_7)$ alkyl group.

4. A compound of formula (1) as claimed in claim 1 in which $R_4$ represents hydrogen and Z represents a cyclo $(C_5-C_8)$alkyl group.

\* \* \* \* \*